(12) United States Patent
Kenmochi

(10) Patent No.: US 7,459,644 B2
(45) Date of Patent: Dec. 2, 2008

(54) DIGITAL MEASUREMENT APPARATUS

(75) Inventor: Hiroki Kenmochi, Tokyo (JP)

(73) Assignee: Tanita Corporation, Tokyo (JP)

( * ) Notice: Subject to any disclaimer, the term of this patent is extended or adjusted under 35 U.S.C. 154(b) by 465 days.

(21) Appl. No.: 11/262,827

(22) Filed: Nov. 1, 2005

(65) Prior Publication Data
US 2006/0096789 A1   May 11, 2006

(30) Foreign Application Priority Data
Nov. 9, 2004   (JP)   ............................. 2004-325149
Aug. 10, 2005  (JP)   ............................. 2005-231448

(51) Int. Cl.
G01G 19/00   (2006.01)
G01G 23/01   (2006.01)

(52) U.S. Cl. ........................ 177/1; 702/101; 177/25.13; 177/25.19; 177/185

(58) Field of Classification Search .............. 177/25.16, 177/1, 25.13, 25.19, 185; 702/101
See application file for complete search history.

(56) References Cited

U.S. PATENT DOCUMENTS

| 4,347,903 | A | * | 9/1982  | Yano et al.     | 177/25.13 |
| 4,366,873 | A | * | 1/1983  | Levy et al.     | 177/25.19 |
| 4,379,495 | A | * | 4/1983  | Cocks et al.    | 177/1     |
| 4,423,792 | A | * | 1/1984  | Cowan           | 177/25.19 |
| 4,553,619 | A | * | 11/1985 | Fujinaga        | 177/185   |
| 4,576,244 | A | * | 3/1986  | Zeigner et al.  | 177/245   |
| 4,660,160 | A | * | 4/1987  | Tajima et al.   | 702/173   |
| 4,715,457 | A | * | 12/1987 | Amacher et al.  | 177/1     |
| 5,230,391 | A | * | 7/1993  | Murata et al.   | 177/50    |
| 5,499,457 | A | * | 3/1996  | Weiler et al.   | 33/512    |
| 5,511,571 | A | * | 4/1996  | Adrezin et al.  | 135/66    |
| 6,215,078 | B1 | * | 4/2001  | Torres et al.  | 177/25.15 |
| 6,538,215 | B2 | * | 3/2003  | Montagnino et al. | 177/25.16 |
| 6,617,530 | B1 | * | 9/2003  | Lin            | 177/25.16 |
| 6,956,175 | B1 | * | 10/2005 | Daly et al.    | 177/1     |
| 2003/0226695 | A1 | * | 12/2003 | Mault       | 177/25.16 |
| 2006/0015016 | A1 | * | 1/2006  | Thornton     | 600/300   |

FOREIGN PATENT DOCUMENTS

| JP | 2001-204704 A | 7/2001 |
| JP | 2002-013976 A | 1/2002 |

* cited by examiner

Primary Examiner—Randy W Gibson
(74) Attorney, Agent, or Firm—McDermott Will & Emery LLP

(57) ABSTRACT

Disclosed is a digital measurement apparatus including data capture means operable to continuously capture digital data about a target measurement item, validity determination means operable to compare the captured data with a reference value so as to determine whether all of the captured data are valid, and measurement-value calculation means operable, when all of the captured data are determined to be valid, to calculate a measurement value in accordance with the valid data, which is characterized by further comprising reference-value change means operable to change the reference value. The digital measurement apparatus of the present invention makes it possible to perform a speedy measurement.

4 Claims, 8 Drawing Sheets

DIGITAL MEASUREMENT APPARATUS

TECHNICAL FIELD

The present invention relates to a digital measurement apparatus which comprises data capture means operable to continuously capture digital data about a target measurement item, validity determination means operable to compare the captured data with a reference value so as to determine whether all of the captured data are valid, and measurement-value calculation means operable, when all of the captured data are determined to be valid, to calculate a measurement value in accordance with the valid data.

BACKGROUND ART

Heretofore, there has been known one type of digital measurement apparatus which comprises data capture means operable to continuously capture digital data about a target measurement item, validity determination means operable to compare the captured data with a reference value so as to determine whether all of the captured data are valid, and measurement-value calculation means operable, when all of the captured data are determined to be valid, to calculate a measurement value in accordance with the valid data. Such a digital measurement apparatus includes various digital weight measurement apparatuses targeting at an object's weight as a measurement item, and various body-composition measurement apparatuses targeting at a user's body composition, such as body fat percentage, visceral fat level, muscle mass, estimated bone mass or basal metabolic rate, as a measurement item.

Among the digital weight measurement apparatuses, a conventional digital body-weight measurement apparatus targeting at a user's body weight is generally designed as follows. When a user steps onto a loading board, an electric signal corresponding to a user's body weight is output from a load sensor incorporated in a main unit of the apparatus. This signal is converted to digital data (count values) through a digital conversion circuit incorporated in the main unit. Then, such count values are continuously sent to a calculation device incorporated in the main unit. When given plural number (e.g. eight) of the count values are captured, the calculation device calculates a difference between a maximum one and a minimum one of the count values (or a variation of the count values), and then compares the variation with a predetermined reference value.

In this process, if the variation of the count values is equal to or less than the reference value, it will be determined that all of the captured count values are valid, or the user is on the loading board in a stable measurement posture in view of a small variation in a load imposed on the loading board. Then, the calculation device calculates a measurement value or a body-weight value in accordance with the captured count values at the time when they are determined to be valid. More specifically, the calculation device converts an average value of the eight count values to a measurement value or a body-weight value, and displays the body-weight value on a display device, such as LCD, incorporated in the main unit.

When the variation of the count values is greater than the reference value, one count value is additionally captured, and the oldest one of the eight previously captured count values is substituted with the latest count value. Then, a variation of the eight regrouped count values is calculated, and re-compared with the reference value.

These processes for capturing an additional count value, calculating a variation and comparing with the reference value will be repeatedly performed until a variation of regrouped count values becomes equal to or less than the reference value. This processing using a reference value is widely used in various digital weight measurement apparatuses other than the body-weight measurement apparatus.

The conventional body-composition measurement apparatus targeting at a user's body composition, such as body fat percentage, visceral fat level, muscle mass, estimated bone mass or basal metabolic rate, as a measurement item, is generally designed as follows. A certain current is supplied between two regions of the body of a user to measure a resulting voltage in the body, and a bioelectric impedance value (hereinafter referred to occasionally as "BI value") of the user is calculated based on the measured voltage. Then, the calculated BI value and a personal parameter of the user typically including body height, body weight, age and sexuality are assigned to a predetermined regression formula to calculate an intended body composition.

For the purpose of calculating a BI value of a user, a main unit of the body-composition measurement apparatus incorporates a group of electrodes and a current-feed circuit for feeding a current between at least two regions of the user's body, and a group of electrodes and a voltage measurement circuit for measuring a voltage to be generated under the current supply depending on an impedance of the user's body.

When the user brings two regions (e.g. right and left feet bottoms) of his/her body into contact with the groups of electrodes, a certain current is fed from the current-feed circuit to the user's body, and an electric signal corresponding to a resulting voltage in the user's body is output from the voltage measurement circuit. This electric signal is converted to a digital signal through an analog-digital conversion circuit incorporated in the main unit, and then continuously sent to a calculation device incorporated in the main unit. In accordance with the received digital signal, the calculation device continuously calculates and captures BI values which are digital data about a body composition or a target measurement item. Then, when the number of captured BI values reaches a given value (e.g. eight), each of the captured BI values is compared with an upper reference value and a lower reference value.

As the result of the comparison, if all of the BI values fall within the range of the upper reference value to the lower reference value, it will be determined that all of the captured BI values are valid, or the user is in a stable measurement posture to maintain an adequate contact between the user's body and the groups of electrodes. Thus, a body composition or a measurement value is calculated based on the BI values at the time when they are determined to be valid. More specifically, an average value of the eight BI values are assigned to the aforementioned regression formula to calculate a value of a body composition, such as body fat percentage or visceral fat level, as a target measurement item, and the calculated body composition value is displayed on a display device, such as LCD, incorporated in the main unit.

When either one of the BI values deviates from the range of the upper reference value to the lower reference value, one BI value is additionally captured, and the oldest one of the eight previously captured count values is substituted with the latest count value. Then, each of the eight regrouped count values is re-compared with the upper reference value and the lower reference value.

These processes for capturing an additional BI value and comparing with the upper reference value and the lower reference value will be repeatedly performed until all of captured BI values fall within the range of the upper reference value to the lower reference value.

Refer, for example, to the following Patent Publications 1 and 2 for the aforementioned digital body-weight measurement apparatus and body-composition measurement apparatus.

[Patent Publication 1] Japanese Patent Laid-Open Publication No. 2002-013976

[Patent Publication 2] Japanese Patent Laid-Open Publication No. 2001-204704

DISCLOSURE OF THE INVENTION

As above, in the conventional digital body-weight measurement apparatus, the capture of count values or a body weight measurement will be continued until a variation of captured count values becomes equal to or less than a reference value. In the conventional body-composition measurement apparatus, the capture of BI values or a body composition measurement will be continued until all of captured BI values fall within the range of an upper reference value to a lower reference value. Thus, a user of these apparatuses is often required to maintain a straight and unmoving measurement posture.

Generally, coldness or mental tension is likely to cause body shakes or tremors, so-called "physiological tremor", even in average adults. In particular, elderly persons can have difficulty in maintaining a constant measurement posture for a long time due to muscular weakening. Infants who have just started walking can also have difficulty in maintaining a constant measurement posture for a long time. Thus, when a person, such as an elderly person, who has difficulty in maintaining a straight and unmoving posture, uses the conventional digital body-weight or body-composition measurement apparatus, body shakes or tremors are liable to cause a fluctuation in count values or BI values due to a load variation and/or inadequate contact with electrodes, and an undesirable situation where it takes a long time before obtaining a final measurement result.

Moreover, most of the conventional digital body-weight and body-composition measurement apparatuses are designed to determine as a measurement error a situation where the capture of count values or BI values is continued for an excessively long time, and discontinue the measurement. Thus, a user who has difficulty in maintaining a straight and unmoving measurement posture can fail to obtain any measurement result. In addition to a physical load required for maintaining a straight and unmoving posture, the incapability of learning a body weight or body composition gives such a user a hard time. This is likely to lead avoidance of the use of the body-weight or body-composition measurement apparatus, and cause a problem on health care.

Particularly, the body-composition measurement apparatus using BI values involves the following problem when used by a person of a higher age. In some cases, in conjunction with progress in keratinization of a user's skin due to aging, a calculated BI value becomes larger, or becomes liable to exceed an upper reference value predetermined based on average adults. In other cases, elderly persons are apt to have deterioration in the flow of body fluid, and a formed edema is hardly cured. Due to the presence of edema, a calculated BI value becomes lower, or becomes liable to fall below a lower reference value predetermined based on average adults. These factors result in occurrence of a measurement error during use of the body-composition measurement apparatus by an elderly person.

In the conventional digital body-weight measurement apparatuses, count values are apt to become more unstable as a body weight to be measured is increased. Specifically, an overweight person generally has difficulty in maintaining a straight and unmoving measurement posture, and the person's body is apt to shake on the body-weight measurement apparatus to cause a larger load variation. While such body shakes can be suppressed as long as a person has muscles required for maintaining an adequate measurement posture even if he/she is overweight, a fattish person who is overweight not due to excessive muscles but due to excessive fat is likely to have difficulty in suppressing body shakes, resulting in an extended measurement time or occurrence of a measurement error.

The conventional digital body-weight measurement apparatuses also include one type equipped with a cradle for use in baby's growth management (so called "baby scale"), and this type apparatus has been increasingly being used in medical centers and homes. Babies express discomforts, such as hunger, hotness and coldness, by crying, and often move his/her body even in a normal situation without crying. Thus, during a baby's body-weight measurement using the baby scale, measured count values are apt to become unstable, resulting in an extended measurement time or occurrence of a measurement error.

If a user has disease, injury or fatigue, the need for maintaining a straight and unmoving posture is likely to cause bafflement to or impose a heavy burden on the user. Thus, during a body weight measurement using the conventional digital body-weight measurement apparatus, a measurement time is apt to become longer, or the risk of a measurement error is apt to be increased.

If a floor has an uneven surface or receives vibrations from surroundings when the conventional digital weight or body-weight measurement apparatus is placed thereon, measured count values about weight are apt to become unstable, resulting in an extended measurement time or occurrence of a measurement error.

It is therefore an object of the present invention to provide a digital measurement apparatus capable of solving the above conventional problems.

In order to achieve the above object, the present invention provides a digital measurement apparatus including data capture means operable to continuously capture digital data about a target measurement item, validity determination means operable to compare the captured data with a reference value so as to determine whether all of the captured data are valid, and measurement-value calculation means operable, when all of the captured data are determined to be valid, to calculate a measurement value in accordance with the valid data, which is characterized by further comprising reference-value change means operable to change the reference value.

In the digital measurement apparatus of the present invention, the target measurement item may be weight, particularly a body weight or body composition of a user.

In the digital measurement apparatus of the present invention, when the target measurement item is a body weight or body composition of a user, the reference-value change means may include at least age-information acquisition means for acquiring information about user's age. In this case, the reference-value change means is preferably operable to change the reference value in accordance with the acquired age information.

In the above digital measurement apparatus, the reference-value change means is preferably operable, when the user's age contained in the acquired age information is equal to or greater than a given age, to change the reference value.

In the above digital measurement apparatus, the reference-value change means is preferably operable to add or subtract the user's age contained in the acquired age information to or from the reference value so as to obtain an adjusted reference value.

In the digital measurement apparatus of the present invention, when the target measurement item is a body weight of a user, the reference-value change means may include body-weight-information acquisition means for tentatively acquiring information about user's body weight in accordance with the digital data captured by the data capture means. In this case, the reference-value change means is preferably operable to change the reference value in accordance with the tentatively acquired body-weight information.

In the above digital measurement apparatus, the reference-value change means is preferably operable, when the user's body weight contained in the tentatively acquired body-weight information is equal to or greater than a given value, to change the reference value.

In the above digital measurement apparatus, the reference-value change means is preferably operable to add the user's body weight contained in the tentatively acquired body-weight information to the reference value so as to obtain an adjusted reference value.

In the digital measurement apparatus of the present invention, when the target measurement item is weight or a body weight of a user, the reference-value change means may include elapsed-time-information acquisition means for acquiring information about an elapsed time from initiation of the digital data capturing operation by the data capture means. In this case, the reference-value change means is preferably operable to change the reference value in accordance with the acquired elapsed-time information.

In the above digital measurement apparatus, the reference-value change means is preferably operable to add the elapsed time contained in the acquired elapsed-time information to the reference value so as to obtain an adjusted reference value.

In the digital measurement apparatus of the present invention, the reference-value change means may include change-intention entry means for allowing a user to enter a command indicative of a user's intention of changing the reference value. In this case, the reference-value change means is preferably operable, in response to the entered user's intention command, to change the reference value.

The digital measurement apparatus of the present invention is provided with the reference-value change means operable to change the reference value for use in determining the validity of the captured data. Thus, when a user or object is likely to be unable to allow the captured data to have a variation range equal to or less than the reference value or to totally fall within the range of the reference value, and thereby likely to have incompletion of the measurement or occurrence of a measurement error, the reference value can be changed by the reference-value change means, so as to complete the measurement or avoid the measurement error.

In particular, when the target measurement item is a body weight or body composition of a user, the reference-value change means may include at least the age-information acquisition means for acquiring information about user's age, and the reference-value change means may be designed to change the reference value in accordance with the acquired age information. This makes it possible to perform a speedy measurement using an appropriate reference value adjusted depending on user's ages.

Further, the reference-value change means may be designed to change the reference value when the user's age contained in the acquired age information is equal to or greater than a given age. In this case, an original reference value can be applied to an average adult of an age less than the given age, to perform the measurement with a high degree of accuracy. Further, as for an elderly person who has difficulty in maintaining a measurement posture, the original reference value can be changed to have a lager value or a wider range, to absorb adverse affects of load variations and/or inadequate contact with electrodes due to body shakes or tremors so as to quickly complete the measurement.

Furthermore, the reference-value change means may be designed to add or subtract the user's age contained in the acquired age information to or from the reference value so as to obtain an adjusted reference value. This makes it possible to change the reference value depending on user's ages in a significantly simple manner.

Alternatively, when the target measurement item is a body weight of a user, the reference-value change means may include body-weight-information acquisition means for tentatively acquiring information about user's body weight in accordance with the digital data captured by the data capture means, and the reference-value change means may be designed to change the reference value in accordance with the tentatively acquired body-weight information. This makes it possible to perform a speedy measurement using a tentative reference value adjusted depending on user's approximate body weights.

Further, the reference-value change means may be designed to change the reference value when the user's body weight contained in the tentatively acquired body-weight information is equal to or greater than a given value. In this case, an original reference value can be applied to a user having a body weight less than the given value, to perform the measurement with a high degree of accuracy. Further, as for a user who has a body weight equal to or greater than the given value or has difficulty in maintaining a measurement posture due to overweight, the original reference value can be changed to a lager value, to absorb adverse affects of load variations due to body shakes or tremors so as to quickly complete the measurement.

Furthermore, the reference-value change means may be designed to add the user's body weight contained in the tentatively acquired body-weight information to the reference value so as to obtain an adjusted reference value. This makes it possible to change the reference value depending on user's approximate body weights in a significantly simple manner.

Alternatively, when the target measurement item is weight or a body weight of a user, the reference-value change means may include elapsed-time-information acquisition means for acquiring information about an elapsed time from initiation of the digital data capturing operation by the data capture means, and the reference-value change means may be designed to change the reference value in accordance with the acquired elapsed-time information. This makes it possible to perform a speedy measurement using a reference value adjusted depending on elapsed times from initiation of the measurement. This means that the reference value can be changed without being based on individual characteristics of users or objects. For example, a highly accurate measurement can be performed using an original reference value regardless of age or body weight as long as a user is capable of maintaining an adequate measurement posture. Further, such a measurement can be appropriately performed even in the situation where measured count values about weight are otherwise apt to become unstable due to external environments, such as uneven surface or vibrations of a floor having the digital measurement apparatus placed thereon.

Further, the reference-value change means may be designed to add the elapsed time contained in the acquired elapsed-time information to the reference value so as to obtain an adjusted reference value. This makes it possible to change the reference value depending on elapsed times from initiation of the measurement in a significantly simple manner.

In the digital measurement apparatus of the present invention, the reference-value change means may include the change-intention entry means for allowing a user to enter a command indicative of a user's intention of changing the reference value, and the reference-value change means may be designed to change the reference value in response to the entered user's intention command. In this case, the user can freely change the reference value depending on surrounding environments or the like.

Other features and advantages of the present invention will be apparent from the accompanying drawings and from the detailed description.

BEST MODE FOR CARRYING OUT THE INVENTION

Figure 1:
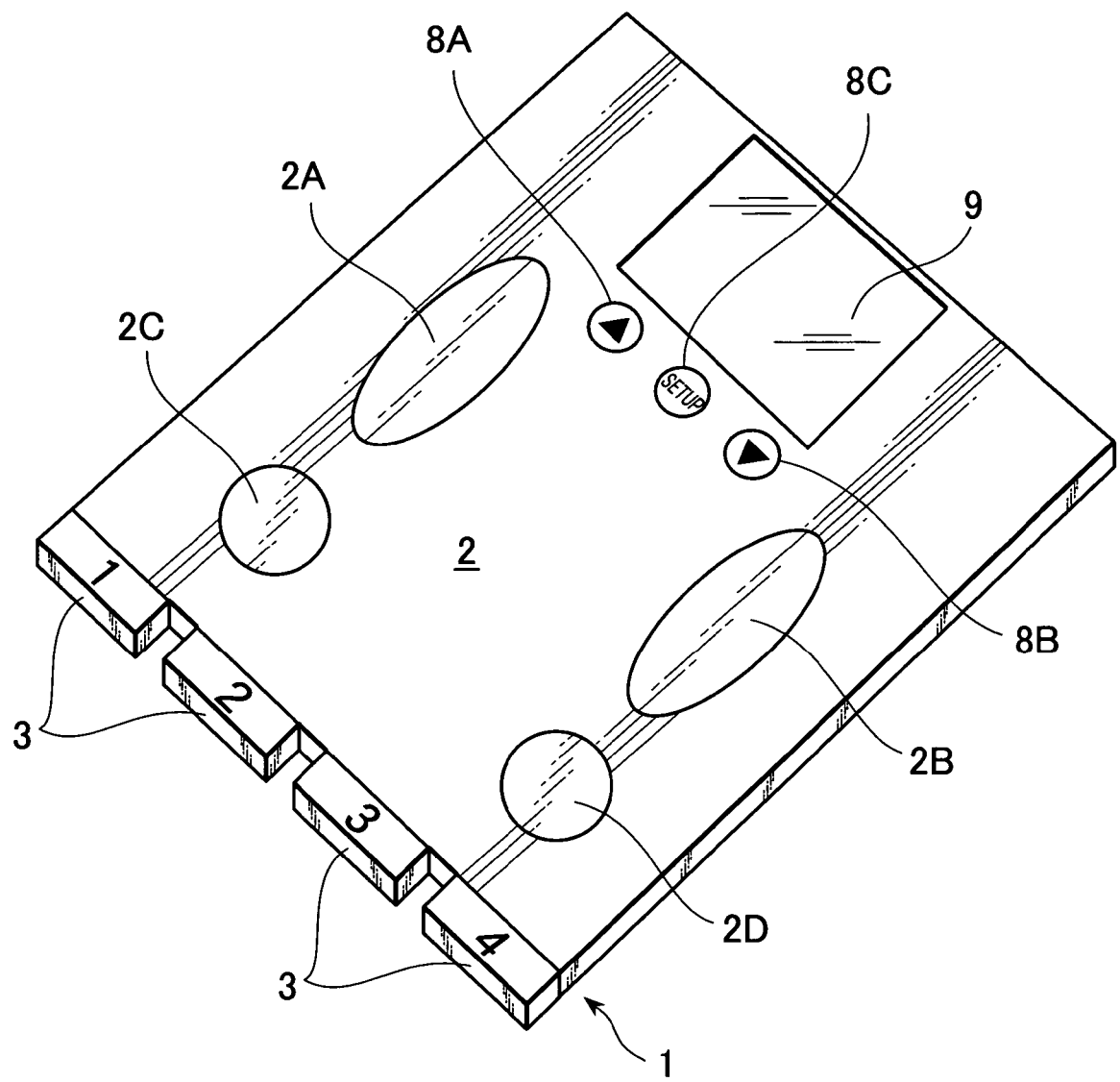
FIG. 1 is a schematic perspective external view showing a digital measurement apparatus 1 according to a first embodiment of the present invention.

In a digital measurement apparatus including data capture means operable to continuously capture digital data about a target measurement item, validity determination means operable to compare the captured data with a reference value so as to determine whether all of the captured data are valid, and measurement-value calculation means operable, when all of the captured data are determined to be valid, to calculate a measurement value in accordance with the valid data, the present invention is characterized by further comprising reference-value change means operable to change the reference value.

In the digital measurement apparatus of the present invention, the target measurement item may be weight, particularly a body weight or body composition of a user.

In the digital measurement apparatus of the present invention, when the target measurement item is a body weight or body composition of a user, the reference-value change means may include at least age-information acquisition means for acquiring information about user's age. In this case, the reference-value change means is preferably operable to change the reference value in accordance with the acquired age information.

In the above digital measurement apparatus, the reference-value change means is preferably operable, when the user's age contained in the acquired age information is equal to or greater than a given age, to change the reference value.

In the above digital measurement apparatus, the reference-value change means is preferably operable to add or subtract the user's age contained in the acquired age information to or from the reference value so as to obtain an adjusted reference value.

In the digital measurement apparatus of the present invention, when the target measurement item is a body weight of a user, the reference-value change means may include body-weight-information acquisition means for tentatively acquiring information about user's body weight in accordance with the digital data captured by the data capture means. In this case, the reference-value change means is preferably operable to change the reference value in accordance with the tentatively acquired body-weight information.

In the above digital measurement apparatus, the reference-value change means is preferably operable, when the user's body weight contained in the tentatively acquired body-weight information is equal to or greater than a given value, to change the reference value.

In the above digital measurement apparatus, the reference-value change means is preferably operable to add the user's body weight contained in the tentatively acquired body-weight information to the reference value so as to obtain an adjusted reference value.

In the digital measurement apparatus of the present invention, when the target measurement item is weight or a body weight of a user, the reference-value change means may include elapsed-time-information acquisition means for acquiring information about an elapsed time from initiation of the digital data capturing operation by the data capture means.

In this case, the reference-value change means is preferably operable to change the reference value in accordance with the acquired elapsed-time information.

In the above digital measurement apparatus, the reference-value change means is preferably operable to add the elapsed time contained in the acquired elapsed-time information to the reference value so as to obtain an adjusted reference value.

In the digital measurement apparatus of the present invention, the reference-value change means may include change-intention entry means for allowing a user to enter a command indicative of a user's intention of changing the reference value. In this case, the reference-value change means is preferably operable, in response to the entered user's intention command, to change the reference value.

With reference to the drawings, a preferred embodiment of the present invention will now be described.

FIRST EMBODIMENT

Figure 2:
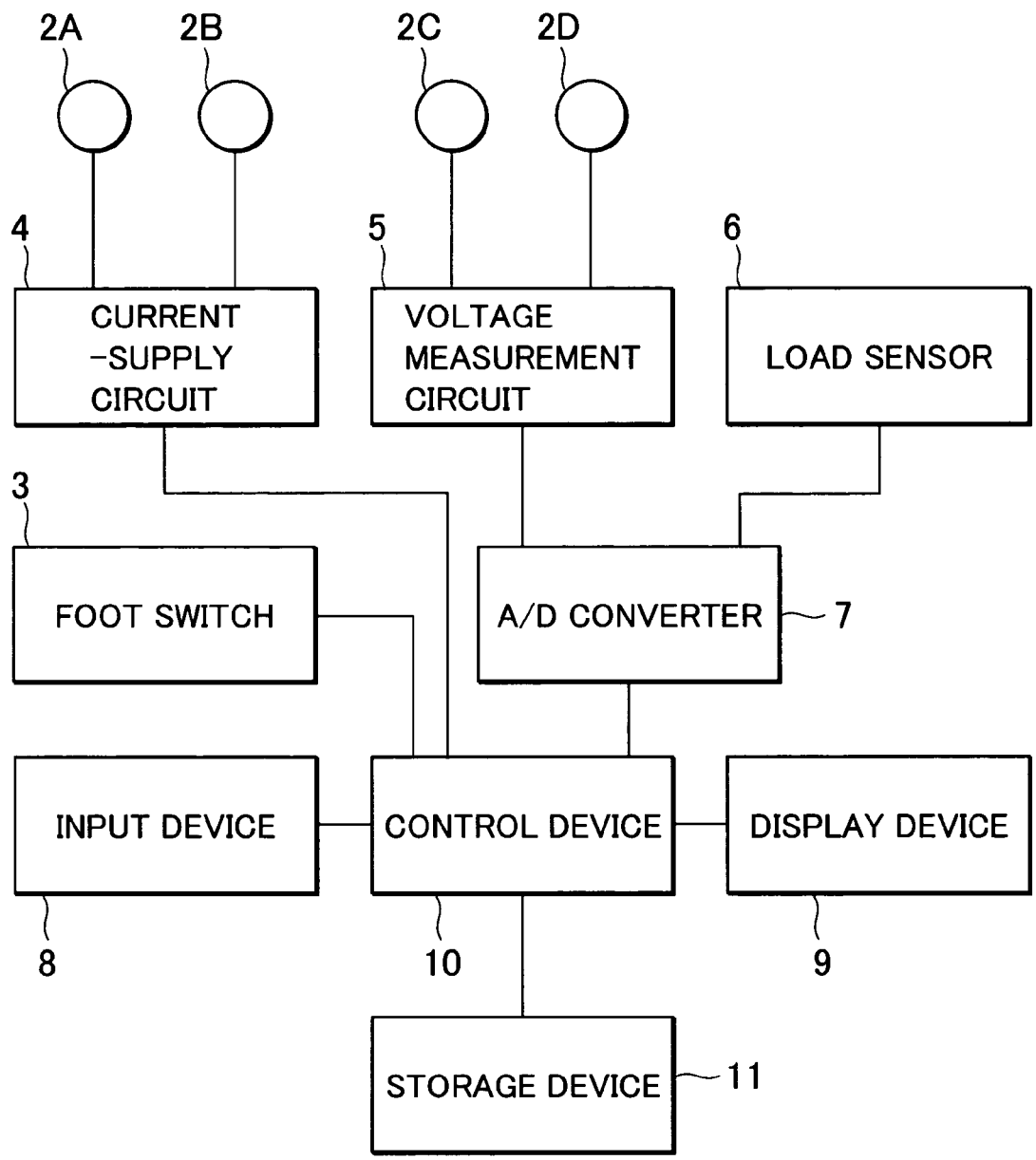
FIG. 2 is a schematic block diagram showing the configuration of an electric circuit incorporated in the digital measurement apparatus 1.
Figure 3:
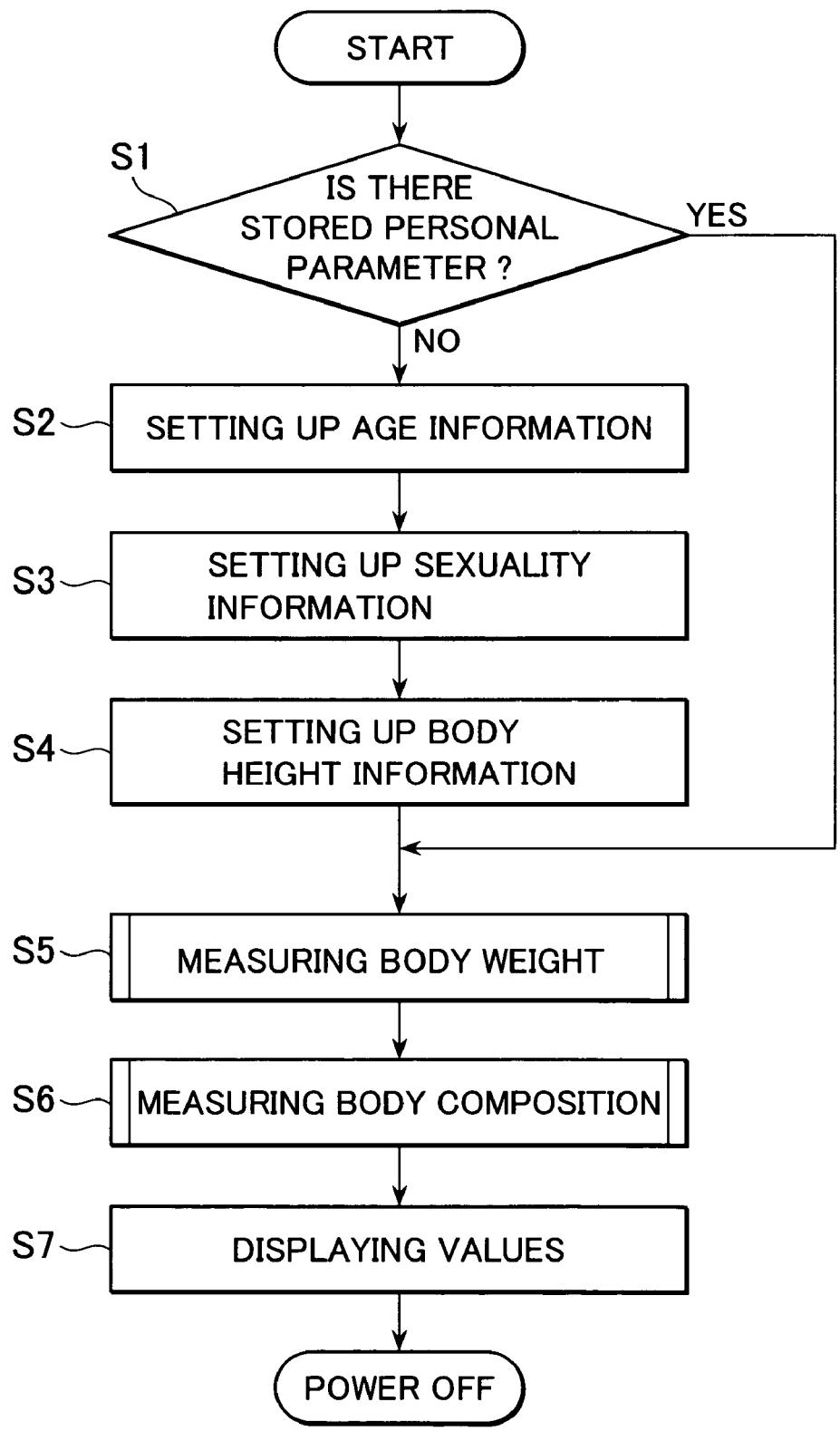
FIG. 3 is a flowchart showing a main control routine to be performed in the digital measurement apparatus 1.
Figure 4:
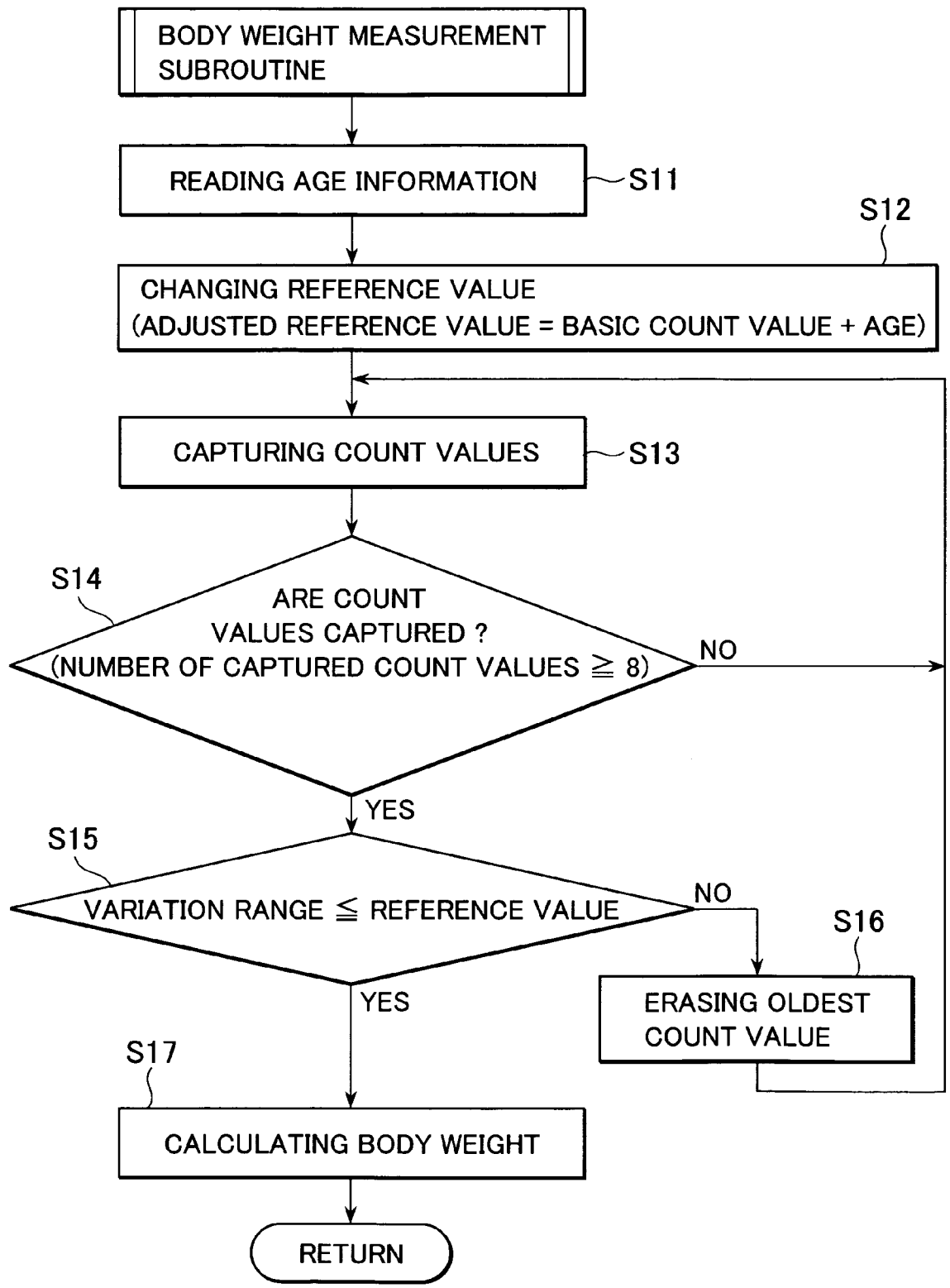
FIG. 4 is a flowchart showing a body-weight measurement control subroutine to be performed in the digital measurement apparatus 1.
Figure 5:
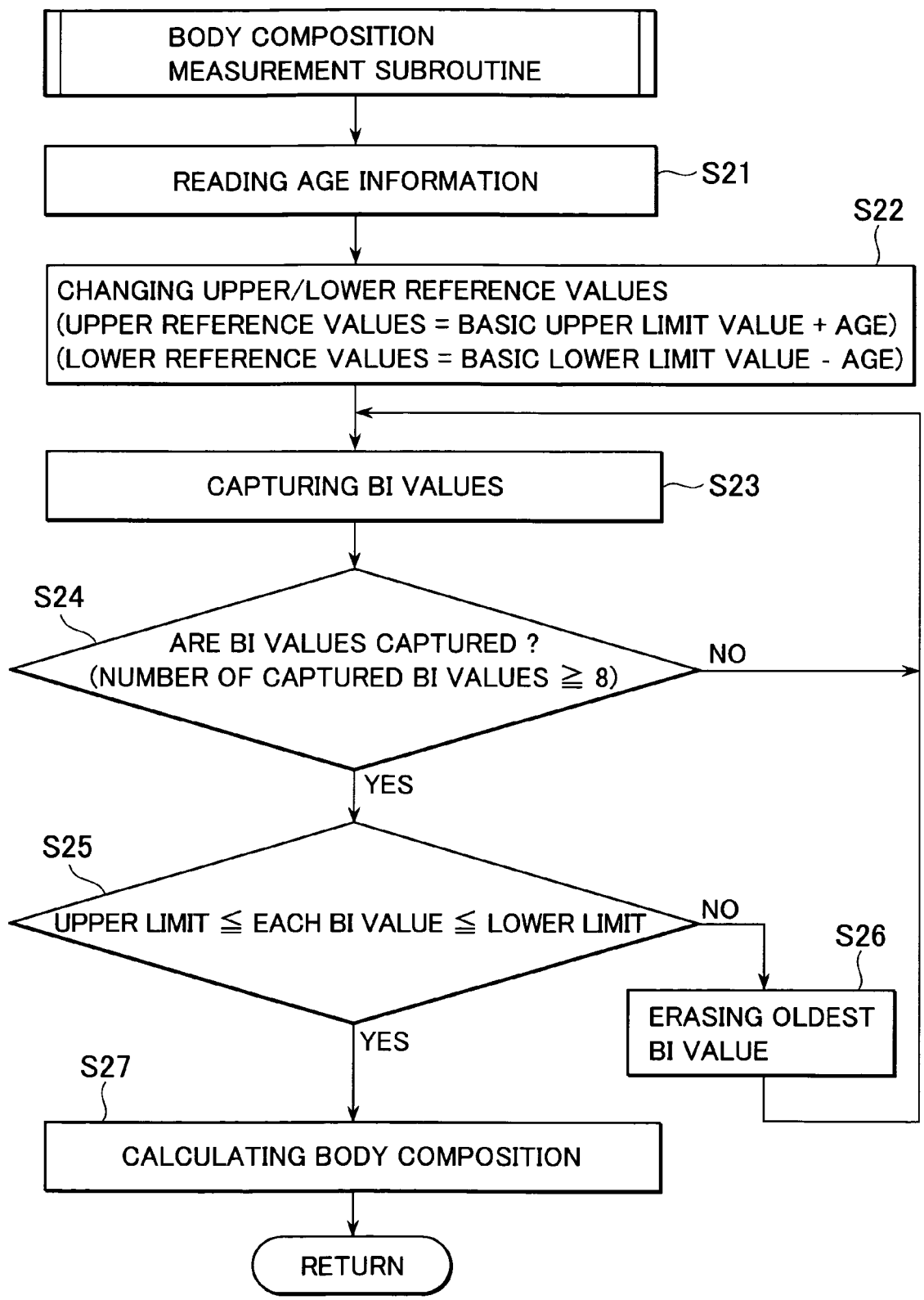
FIG. 5 is a flowchart showing a body-composition measurement control subroutine to be performed in the digital measurement apparatus 1.

A first embodiment of the present invention will be described below. FIG. 1 is a schematic perspective external view showing a digital measurement apparatus 1 according to a first embodiment of the present invention. FIG. 2 is a schematic block diagram showing the configuration of an electric circuit incorporated in the digital measurement apparatus 1, and FIG. 3 is a flowchart showing a main control routine to be performed in the digital measurement apparatus 1. FIG. 4 is a flowchart showing a body-weight measurement control subroutine to be performed in the digital measurement apparatus 1, and FIG. 5 is a flowchart showing a body-composition measurement control subroutine to be performed in the digital measurement apparatus 1.

This digital measurement apparatus 1 (hereinafter referred to as "apparatus 1" for brevity) is fundamentally obtained by making substantial improvements in a conventional body-composition analyzer or measurement apparatus designed to measure a body weight of a user and calculate a body composition of the user, such as body fat percentage, visceral fat level, body water percentage, muscle mass, estimated bone mass or basal metabolic rate, by use of BI values between the feet of the user. As shown in FIG. 1, the digital measurement apparatus 1 has a main unit 2 with a top surface serving as a loading board. The top surface of the main unit 2 is provided with a pair of current-supply electrodes 2A, 2B for supplying an AC current between the right and left feet bottoms of a user, a pair of measurement electrodes 2C, 2D for measuring a resulting voltage (potential difference) between the right and left feet bottoms, an input device 8 including an up-switch 8A, a down-switch 8B and a setup switch 8C to enter a personal parameter of the user, such as age, sexuality or body height, and a display device 9 for displaying body-weight and body-composition values measured by the apparatus 1 and other information. The main unit 2 has a side surface provided with four foot switches 3 for calling up a registered personal parameter if any. Each of the foot switches 3 also serves as a power-on switch.

As shown in FIG. 2, the main unit 2 of the apparatus 1 internally includes a current-feed circuit 4 electrically connected to the current-supply electrodes 2A, 2B to feed a high-frequency constant current to these electrodes 2A, 2B, a voltage measurement circuit 5 electrically connected to the measurement electrodes 2C, 2D to output an electric signal corresponding to a voltage generated between these electrodes 2C, 2D, a load sensor 6 for outputting an electric signal corresponding to a load, or a body weight of the user, imposed on the top surface of the main unit 2, an A/D converter 7 for concerting each of the analog electric signals from the voltage measurement circuit 5 and the load sensor 6 to a digital signal, a calculation device 10 for calculating a body-weight value and a body-composition value, and a storage device 11 for storing the personal parameter, the calculated body-weight and body-composition values, and other information or data. The control device 10 is electrically connected to each of the current-feed circuit 4, the A/D converter 7, the storage device 11, the input device 8, the display device 9 and the foot switches 3.

The control device 10 is provided with a conventional calculation element (CPU), and designed to execute a control program pre-stored on the storage device 11 so as to perform a control routine including various control subroutines for: receiving an input of the personal parameter from the input device 8; calculating a body-weight value of the user in accordance with a count value captured from the load sensor 6 through the A/D converter 7; supplying a high-frequency constant current to the current-supply electrodes 2A, 2B and concurrently calculating a BI value of the user in accordance with a digital signal entered from the measurement electrodes 2C, 2D through the voltage measurement circuit 5 and the A/D converter 7; calculating a body-composition value of the user in accordance with the personal parameter, the body-weight value and the BI value; and displaying the calculated weight-value and body-composition values on the display device 9 and storing these values on the storage device 11.

The flowchart illustrated in FIG. 3 shows a main control routine to be performed in the control device 1 when a user uses the apparatus 1. When the user pushes down either one of the foot switches 3 to activate the apparatus 1, this main control routine is performed.

In Step S1, it is determined whether a personal parameter is stored on one of a plurality of data blocks of the storage device 11, which is secured in association with a number assigned to the pushed foot switches 3. When no personal parameter is stored, the process advances to Step S2. If the personal parameter is stored, the process will skip Steps S2 to S4 to advance directly to Step S5.

In Step S2, information about user's age is set up or acquired. Specifically, a certain numerical value indicative of age is automatically displayed on the display device 9. The user increases or reduces this numerical value using the up-switch 8A or the down-switch 8B to match the numerical value and his/her age, and then pushes down the setup switch 8C. Then, the setup value is stored as the user's age on the data block associated with the number of the currently pushed foot switch 3. When the apparatus 1 is equipped with a clock capable of keeping the current date or has a calendar function, Step S2 may be configured to allow the user to enter his/her birth date, and calculate the user's age in accordance with the current date and the entered birth date.

Then, in Step S3, information about sexuality of the user is entered. Specifically, selection characters or marks indicative of mail and female are automatically displayed on the display device 9. The user selects his/her sexuality using the up-switch 8A and/or the down-switch 8B, and sets up the selected sexuality using the setup switch 8C. Then, in Step S4, information about body height of the user is entered. Specifically, a certain numerical value indicative of body height is automatically displayed on the display device 9. The user increases or reduces this numerical value using the up-switch 8A or the down-switch 8B to match the numerical value and his/her body height, and sets up the adjusted value using the setup switch 8C. As with the information about age, the information about sexuality and body height are stored on the data block associated with the number of the currently pushed foot switch 3.

In Step S5, an after-mentioned body-weight measurement control subroutine is performed, or a body-weight value is calculated and stored. In Step S6, an after-mentioned body-composition measurement control subroutine is performed, or a body-composition value is calculated and stored. Then, in Step S7, the body-weight and body-composition values calculated and stored in Steps S5 and S6 are displayed on the display device 9. After a lapse of a given time, a power is automatically cut off to complete the entire control routine.

The flowchart illustrated in FIG. 4 shows a body-weight measurement control subroutine to be performed in the above Step S5. In Step S11, the information about user's age is read from the personal parameters stored on the storage device 11 in association with the number of the currently pushed foot switch 3.

Then, Step S12, based on the read information about user's age, a reference value is set up or changed in the following manner. The apparatus 1 is equivalent to a digital body-weight measurement apparatus having a weighing capacity of 100 kg, a minimum unit of 1 kg and 10,000 counts at a full span. In the apparatus 1, a reference value for determining the validity of a variation range of count values is normally set at 50 counts (hereinafter referred to as "basic count value"). In this embodiment, the apparatus 1 is designed to add the user's age to the basic count value so as to change the reference value or obtain an adjusted reference value. That is, "an adjusted reference value=the basic count value+the user's age". For example, given that the user's age is 60, an adjusted reference value=50+60=110 counts. The capability of changing the reference value allows the validity of a variation range of count values to be determined under a slightly relaxed condition, or makes it possible to absorb a certain level of load variation due to body shakes or tremors arising from aging so as to perform a speedy body-weight measurement. This Step S12 may be configured to be skipped when the user's age is less than a given age, for example, to be performed only if the user's age is equal to or greater than 55.

Then, in Steps S13 and S14, an electric signal from the load sensor 6 is converted to digital data (count values) through the A/D converter 7, and a maximum of eight count values are continuously captured by the control device 10. More specifically, the count values are captured in Step S13, and it is determined whether the number of captured count values reaches eight, in Step S14. When it is determined that the number of captured count values reaches eight, the process advances to Step S15. If the determination in Step 14 is No, the process will return to Step S13.

Then, in Step S15, a difference between a maximum one and a minimum one of the captured count values is calculated as a variation range, and this variation range is compared with the reference value set up or changed in Step S12. When the variation range is equal to or less than the reference value, all of the captured count values are determined to be valid. That is, it is determined that the variation of a load imposed on the loading board falls within an acceptable range or the user on the loading board is in an approximately stable measurement posture. Then, the process advances to Step S17. If the variation range exceeds the reference value, the process will advance to Step S16. In Step S16, the oldest (earliest or first captured) one of the captured count values is erased, and then the process returns to Step S13. Thus, until a variation range of regrouped count values is determined to be equal to or less than the reference value, the process of Steps S13 to S16 will be repeatedly performed.

Then, in Step S17, an average value of the eight captured count values is calculated, and then converted to a body-weight value. This body-weight value is stored on the data block associated with the number of the currently pushed foot switch 3, together with the personal parameters.

The flowchart illustrated in FIG. 5 shows a body-composition measurement control subroutine to be performed in the aforementioned Step S6. In Step S21, the personal parameters stored on the storage device 11 in association with the number of the currently pushed foot switch 3 is read out.

Then, in Step S22, based on the information about user's age in the read parameters, the reference value is set up or changed in the following manner. In the apparatus 1, a normal reference value for determining whether a contact between the user's feet bottoms and the electrodes 2A, 2B, 2C, 2d is adequate, consists of an upper reference value set at 1,000Ω (hereinafter referred to as "basic upper limit value"), and a lower reference value set at 200Ω (hereinafter referred to as "basic lower limit value"). In this embodiment, the apparatus 1 is designed to add the user's age to the basic upper limit value, and subtract the user's age from the basic lower limit value, so as to change the reference value or obtain an adjusted reference value. That is, "an adjusted upper reference value=the basic upper limit value+the user's age", and "an adjusted lower reference value=the basic lower limit value—the user's age". For example, given that the user's age is 60, an adjusted upper reference value=1,000+60=1,060Ω, and an adjusted lower reference value=200-60=140Ω. The capability of changing the reference value allows the validity of BI values to be determined under a slightly relaxed condition, or makes it possible to absorb a certain level of inadequate contact between the feet bottoms and the electrodes due to body shakes or tremors so as to perform a speedy body-composition measurement. This Step S22 may be configured to be skipped when the user's age is less than a given age, for example, to be performed only if the user's age is equal to or greater than 55.

Then, in Steps S23 and S24, an electric signal from the voltage measurement circuit 5 is converted to a digital signal through the A/D converter 7, and continuously sent to the control device 10. Then, based on the digital signal, a maximum of eight BI values are continuously calculated and captured by the control device 10. More specifically, the BI values are calculated and captured based on the digital signal in Step S23, and it is determined whether the number of captured BI values reaches eight, in Step S24. When it is determined that the number of captured BI values reaches eight, the process advances to Step S25. If the determination in Step 24 is No, the process will return to Step S23.

Then, in Step S25, each of the captured BI values is compared with the upper and lower reference values set up or changed in Step S22. When all of the BI values fall within the range of the upper reference value to the lower reference value, all of the captured BI values are determined to be valid. That is, it is determined that the user is in an approximately stable measurement posture, and the feet bottoms are adequately in contact with the electrodes 2A, 2B, 2C, 2D. Then, the process advances to Step S27. If either one of the BI values deviates from the range of the upper reference value to the lower reference value, the process will advance to Step S26. In Step S26, the oldest (earliest or first captured) one of the captured BI values is erased, and then the process returns to Step S23. Thus, until it is determined that all of the BI values fall within the range of the upper reference value to the lower reference value, in Step S25, the process of Steps S23 to S26 will be repeatedly performed.

Then, in Step S27, an average value of the eight captured BI values is calculated, and then assigned to a predetermined regression formula together with the personal parameters (age, sexuality and body height) read in Step S21 and the body-weight value calculated in Step S5, to calculate an intended body-composition value. The calculated body-composition value is stored on the data block associated with the number of the currently pushed foot switch 3, together with the personal parameters and the body-weight value.

As mentioned above, in this apparatus 1, data capture means operable to capture digital data (count values) about body weight as a target measurement item is primarily composed of the load sensor 6, the A/D converter 7 and the control device 10, or data capture means operable to capture digital data (BI values) about body composition as a target measurement item is primarily composed of the current-supply electrodes 2A, 2B, the measurement electrodes 2C, 2D, the current-feed circuit 4, the voltage measurement circuit 5, the A/D converter 7 and the control device 10. Further, the control device 10 serves as validity determination means operable to compare the variation range of count values or captured data with the reference value, or to compare the BI values or captured data with the upper reference value and the lower reference value, so as to determine whether all of the captured data are valid, measurement-value calculation means operable, when all of the captured data are determined to be valid, to calculate a body-weight or body-composition value as a measurement value in accordance with the valid data, and reference-value change means operable to change the reference value. Furthermore, in the apparatus 1, age-information acquisition means for acquiring information about at least user's age is primarily composed of the input device 8 and the control device 10.

The control device 10 serving as the reference-value change means is operable to add the user's age to the basic count value as a predetermined reference value for count values so as to obtain an adjusted reference value. Further, the control device 10 serving as the reference-value change means is operable to add the user's age to the basic upper limit value as a predetermined reference value for BI values, and subtract the user's age from the basic lower limit value as a predetermined reference value for BI values, so as to obtain an adjusted reference value.

Thus, this apparatus 1 can change the reference value depending on the user's age in a significant simple manner or by adding or subtracting the user's age to or from the predetermined reference value, so as to absorb adverse affects of load variations or inadequate contact with the electrodes due to body shakes or tremors to avoid a measurement error and quickly compete the measurement.

SECOND EMBODIMENT

Figure 6:
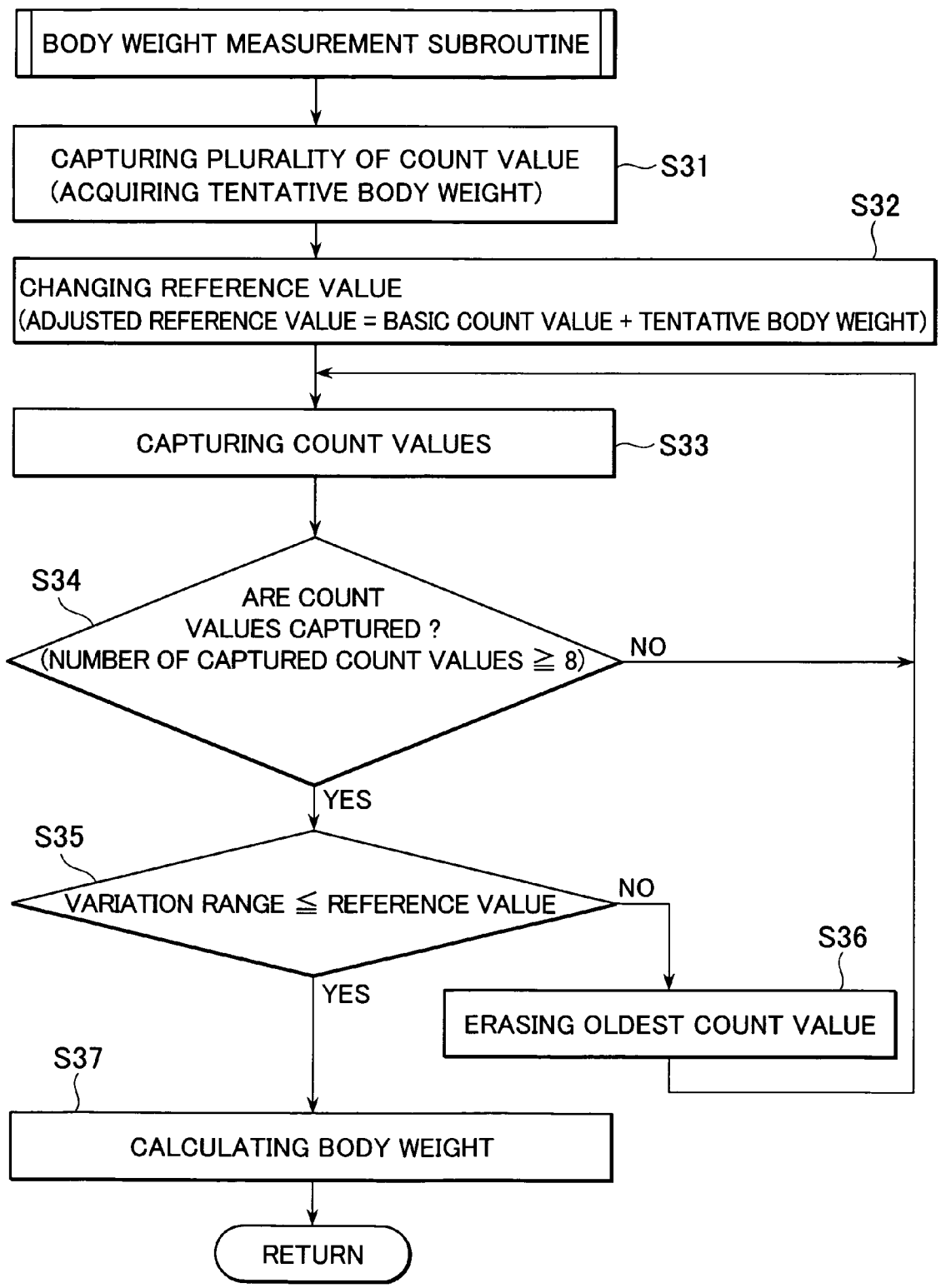
FIG. 6 is a flowchart showing a body-weight measurement control subroutine to be performed in a digital measurement apparatus according to a second embodiment of the present invention.

A second embodiment of the present invention will be described below. Except for a body-weight measurement control subroutine, a digital measurement apparatus according to the second embodiment is identical to the apparatus 1 according to the first embodiment. Thus, the following description will be made only for this body-weight measurement control subroutine, and descriptions on hardware components and the remaining measurement control will be omitted. FIG. 6 is a flowchart showing the body-weight measurement control subroutine to be performed in the digital measurement apparatus according to the second embodiment. In this embodiment and after-mentioned embodiments, the hardware components are defined by the same reference numerals as those in the first embodiment.

Firstly, in Step S31, an electric signal from the load sensor 6 is converted to digital data (count values) through the A/D converter 7, and a maximum of four count values are continuously captured by the control device 10. Then, an average value of the four captured count values is converted to a body-weight value. While this body-weight value is a tentative value acquired in accordance with count values which are not fully-reliable data or not data assured by comparison with a given reference value, it can be considered as an approximate value of user's body weight.

Then, in Step 32, based on the tentatively acquired user's body weight, a reference value is set up or changed in the following manner. As described in the first embodiment, this apparatus is equivalent to a digital body-weight measurement apparatus having a weighing capacity of 100 kg, a minimum unit of 1 kg and 10,000 counts at a full span. In the apparatus, a reference value (basic count value) for determining the validity of a variation range of count values is normally set at 50 counts. In this embodiment, the apparatus is designed to add the tentatively acquired user's body weight to the basic count value so as to change the reference value or obtain an adjusted reference value. That is, "an adjusted reference value=the basic count value+the tentatively acquired user's body weight". For example, given that the tentatively acquired user's body weight (kg) is 80, an adjusted reference value=50+80=130 counts. The capability of changing the reference value allows the validity of a variation range of count values to be determined under a slightly relaxed condition, or makes it possible to absorb a certain level of load variation due to body shakes or tremors arising from over-weight so as to perform a speedy body-weight measurement. This Step S32 may be configured to be skipped when the user's body weight is less than a given value, for example, to be performed only if the user's body weight (kg) is equal to or greater than 80.

Then, in Steps S33 and S34, an electric signal from the load sensor 6 is converted to digital data (count values) through the A/D converter 7, and a maximum of eight count values are continuously captured by the control device 10. More specifically, the count values are captured in Step S33, and it is determined whether the number of captured count values reaches eight, in Step S34. When it is determined that the number of captured count values reaches eight, the process advances to Step S35. If the determination in Step 34 is No, the process will return to Step S33.

Then, in Step S35, a difference between a maximum one and a minimum one of the eight captured count values is calculated as a variation range, and this variation range is compared with the reference value set up or changed in Step S32. When the variation range is equal to or less than the reference value, all of the captured count values are determined to be valid. That is, it is determined that the variation of a load imposed on the loading board falls within an acceptable range or the user on the loading board is in an approximately stable measurement posture. Then, the process advances to Step S37. If the variation range exceeds the reference value, the process will advance to Step S36. In Step S36, the oldest (earliest or first captured) one of the captured count values is erased, and then the process returns to Step S33. Thus, until a variation range of regrouped count values is determined to be equal to or less than the reference value, in Step S 35, the process of Steps S33 to S36 will be repeatedly performed.

Then, in Step S37, an average value of the eight captured count values is calculated, and then converted to a body-weight value. This body-weight value is stored on the data block associated with the number of the currently pushed foot switch 3, together with the personal parameters.

As mentioned above, in the apparatus according to the second embodiment, data capture means operable to capture digital data (count values) about body weight as a target measurement item is primarily composed of the load sensor 6, the A/D converter 7 and the control device 10. Further, the control device 10 serves as validity determination means operable to compare the variation range of count values or captured data with the reference value so as to determine whether all of the captured data are valid, measurement-value calculation means operable, when all of the captured data are determined to be valid, to calculate a body-weight as a measurement value in accordance with the valid data, and reference-value change means operable to change the reference value. Furthermore, body-weight-information acquisition means for tentatively acquiring information about user's body weight is primarily composed of the load sensor 6, the A/D converter 7 and the control device 10.

The control device 10 serving as the reference-value change means is operable to add the tentatively acquired user's body weight to the basic count value as a predetermined reference value for count values so as to obtain an adjusted reference value.

Thus, the apparatus according to the second embodiment can change the reference value depending on user's approximate body weights in a significant simple manner so as to absorb adverse affects of load variations due to body shakes or tremors through the use of an adjusted reference value based on the user's approximate body weight to avoid a measurement error and quickly compete the measurement.

THIRD EMBODIMENT

Figure 7:
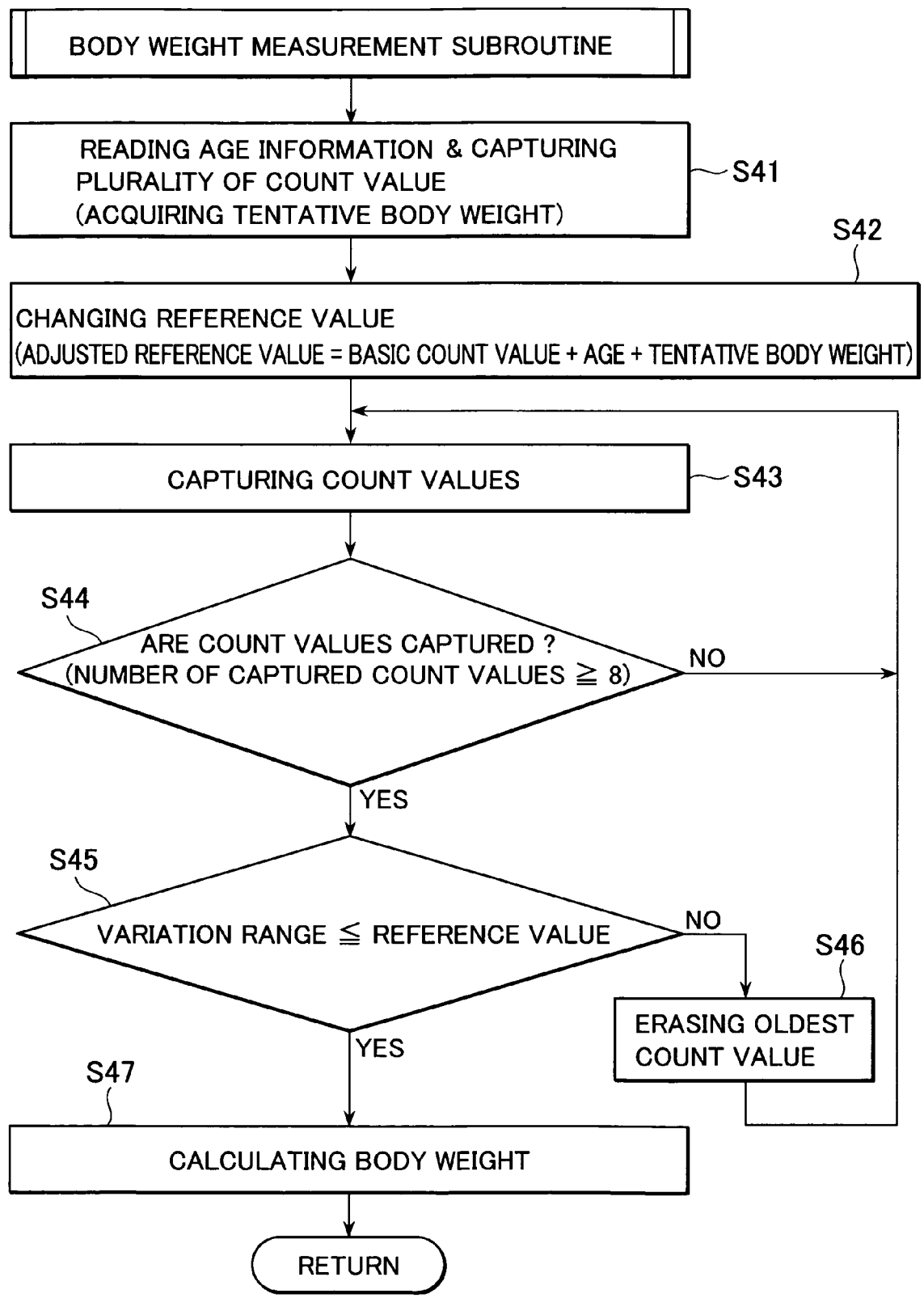
FIG. 7 is a flowchart showing a body-weight measurement control subroutine to be performed in a digital measurement apparatus according to a third embodiment of the present invention.

A third embodiment of the present invention will be described below. Except for a body-weight measurement control subroutine, a digital measurement apparatus according to the third embodiment is identical to the apparatus 1 according to the first embodiment. Thus, the following description will be made only for this body-weight control subroutine, and descriptions on hardware components and the remaining measurement control will be omitted. FIG. 7 is a flowchart showing the body-weight measurement control subroutine to be performed in the digital measurement apparatus according to the third embodiment.

Fundamentally, the third embodiment is a combination of the first and second embodiment. Firstly, in Step S41, information about user's age is read from the personal parameters stored on the storage device 11 in association with the number of a currently pushed foot switch 3. Simultaneously, in Step S41, an electric signal from the load sensor 6 is converted to digital data (count values) through the A/D converter 7, and a maximum of four count values are continuously captured by the control device 10. Then, an average value of the four captured count values is converted to a body-weight value.

Then, in Step 42, based on the read user's age and the tentatively acquired user's body weight, a reference value is set up or changed in the following manner. As described in the first embodiment, this apparatus is equivalent to a digital body-weight measurement apparatus having a weighing capacity of 100 kg, a minimum unit of 1 kg and 10,000 counts at a full span. In the apparatus, a reference value (basic count value) for determining the validity of a variation range of count values is normally set at 50 counts. In this embodiment, the apparatus is designed to add the user's age and the tentatively acquired user's body weight to the basic count value so as to change the reference value or obtain an adjusted reference value. That is, "an adjusted reference value=the basic count value+age+the tentatively acquired user's body weight". For example, given that the user's age is 60 and the tentatively acquired user's body weight (kg) is 80, an adjusted reference value=50+60+80=190 counts. The capability of changing the reference value allows the validity of a variation range of count values to be determined under a slightly relaxed condition, or makes it possible to absorb a certain level of load variation due to body shakes or tremors arising from overweight so as to perform a speedy body-weight measurement.

In this Step S42, the contribution rate of the user's parameters for use in changing the reference value may be appropriately arranged to provide enhanced usability. For example, the adjusted reference value may be calculated by adding (the age+the tentatively acquired user's body weight)/2 to the basic count value. Further, the Step S42 may be configured to be skipped when at least one of the user's age and body weight is less than a given value, for example, to be performed only if the user's age is equal to or greater than 55, or the user's body weight (kg) is equal to or greater than 80.

Then, Steps S43 to 47 are the same as Steps S13 to S17 described in connection with FIG. 4 or Steps S33 to S 37 described in connection with FIG. 6. Thus, descriptions of Steps S43 to 47 will be omitted.

FOURTH EMBODIMENT

Figure 8:
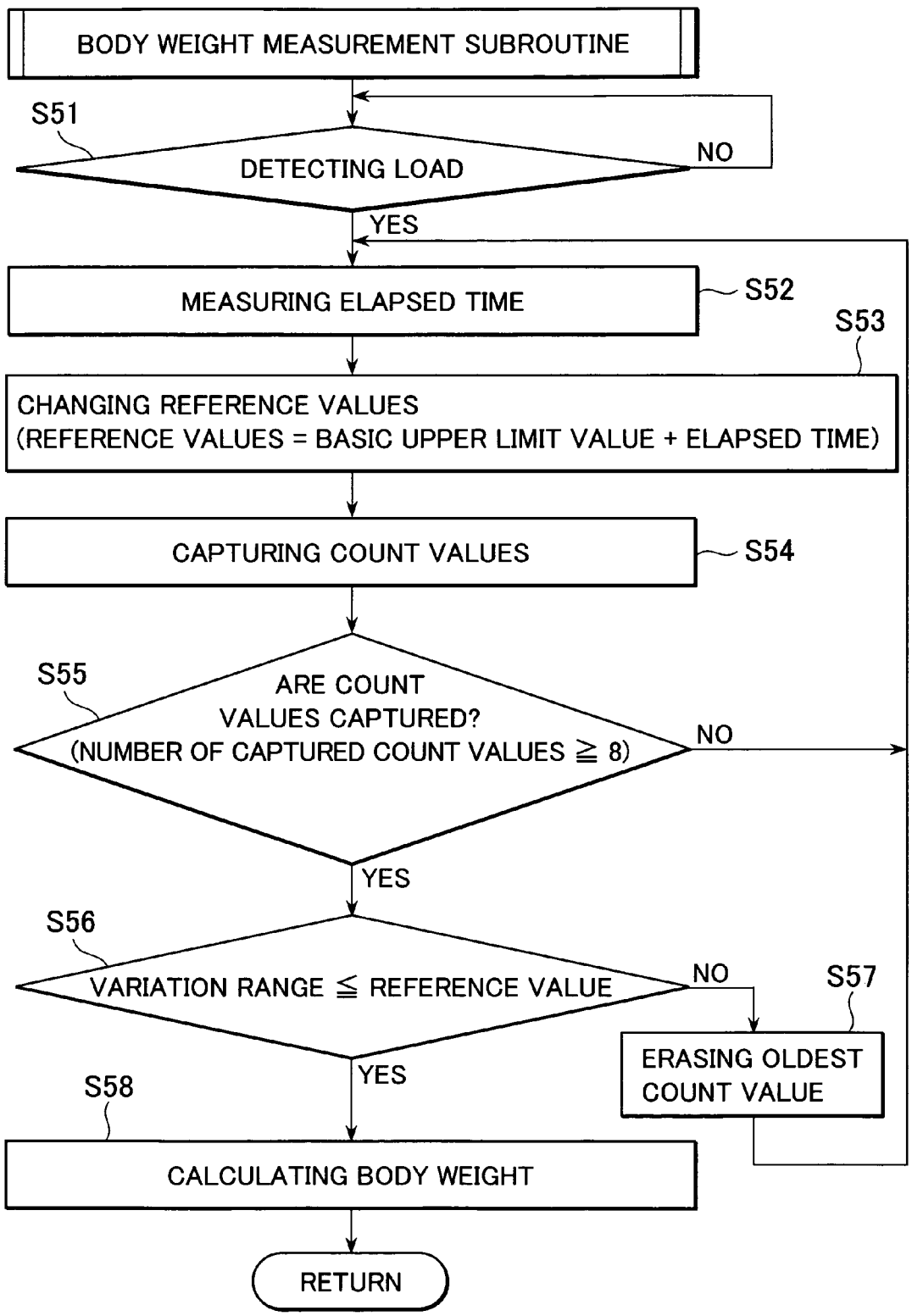
FIG. 8 is a flowchart showing a body-weight measurement control subroutine to be performed in a digital measurement apparatus according to a fourth embodiment of the present invention.

A fourth embodiment of the present invention will be described below. Except for a body-weight measurement control subroutine, a digital measurement apparatus according to the fourth embodiment is identical to the apparatus 1 according to the first embodiment. Thus, the following description will be made only for this body-weight measurement control subroutine, and descriptions on hardware components and the remaining measurement control will be omitted. FIG. 8 is a flowchart showing the body-weight measurement control subroutine to be performed in the digital measurement apparatus according to the fourth embodiment.

Firstly, in Step S51, it is determined whether a load is detected by the load sensor 6 or whether an electric signal is generated from the load sensor 6. When the determination in Step S51 is YES or it is determined that the load is detected, the process advances to Step S52. The electric signal sent from the load sensor 6 and used for the determination in Step S51 is converted to digital data (count values) in after-mentioned Step S54, and captured by the control device 10. That is, the detection of this electric signal in Step S51 means the initiation of a data capturing operation.

Then, in Step S52, an elapsed time is measured by a clock function incorporated in the control device 10. The elapsed time is set to an initial value (zero second) when the process initially advances to Step S52. The elapsed time is measured on the second time scale every time the process passes through Step S52, or the process advances from Step S51 to Step S52 and returns from after-mentioned Step S57 to Step S52 (i.e. the clock function is equivalent to a timer designed to be incremented on the second time scale). Thus, when the process advances from Step S51 to Step S52, the elapsed time is set to zero second and measured as zero second. It is understand that if the process re-passes through Step S52 before an elapse of one second since the last time measurement, the same lapsed time as that in the last time measurement will be re-measured.

Then, in Step 53, based on the elapsed time measured in Step 52, a reference value is set up or changed in the following manner. As described in the first embodiment, this apparatus is equivalent to a digital body-weight measurement apparatus having a weighing capacity of 100 kg, a minimum unit of 1 kg and 10,000 counts at a full span. In the apparatus, a reference value (basic count value) for determining the validity of a variation range of count values is normally set at 50 counts. In this embodiment, the apparatus is designed to add the measured or acquired elapsed time to the basic count value so as to change the reference value or obtain an adjusted reference value. That is, "an adjusted reference value=the basic count value+the acquired elapsed time". For example, when the process initially advances from Step S51 to Step S52, an adjusted reference value=50+0=50 counts. Further, given that the acquired elapsed time (second) is 5 as a result that the after-mentioned process is repeated several times, an adjusted reference value=50+5=55 counts.

Then, in Steps S54 and S55, the electric signal from the load sensor 6 is converted to digital data (count values) through the A/D converter 7, and a maximum of eight count values are continuously captured by the control device 10. More specifically, the count values are captured in Step S54, and it is determined whether the number of captured count values reaches eight, in Step S55. When it is determined that the number of captured count values reaches eight, the process advances to Step S56. If the determination in Step 55 is No, the process will return to Step S52.

Then, in Step S56, a difference between a maximum one and a minimum one of the eight captured count values is calculated as a variation range, and this variation range is compared with the reference value set up or changed in Step S53. When the variation range is equal to or less than the reference value, all of the captured count values are determined to be valid. That is, it is determined that the variation of a load imposed on the loading board falls within an acceptable range or the user on the loading board is in an approximately stable measurement posture. Then, the process advances to Step S58. If the variation range exceeds the reference value, the process will advance to Step S57. In Step S57, the oldest (earliest or first captured) one of the captured count values is erased, and then the process returns to Step S52. Thus, until a variation range of regrouped count values is determined to be equal to or less than the reference value in Step S56, the process of Steps S52 to S57 will be repeatedly performed.

Every time the process of Steps S52 to S57 is repeated, the lapsed time is measured or acquired on the second time scale in Step S52, and the reference value is set up or adjust according to the calculation "an adjusted reference value=the basic count value+the acquired elapsed time" in Step S53. Thus, for example, if the acquired lapsed time (second) since the detection of the electric signal from the load sensor 6 (i.e. the acquired lapsed time from initiation of the digital data capturing operation) is 5, an adjusted reference value=50+5=55 counts, as described above. If the acquired lapsed time (second) is 10, an adjusted reference value=50+10=60 counts. The capability of changing the reference value allows the validity of a variation range of count values to be determined under a slightly relaxed condition depending on elapsed times from initiation of the measurement, so as to perform a speedy body-weight measurement even under the situation where it is otherwise difficult to stabilize variations in count values.

Then, in Step S58, an average value of the eight captured count values is calculated, and then converted to a body-weight value. This body-weight value is stored on the data block associated with the number of the currently pushed foot switch 3, together with the personal parameters.

As mentioned above, in the apparatus according to the fourth embodiment, data capture means operable to capture digital data (count values) about body weight as a target measurement item is primarily composed of the load sensor 6, the A/D converter 7 and the control device 10. Further, the control device 10 serves as validity determination means operable to compare the variation range of count values or captured data with the reference value so as to determine whether all of the captured data are valid, measurement-value calculation means operable, when all of the captured data are determined to be valid, to calculate a body-weight as a measurement value in accordance with the valid data, and reference-value change means operable to change the reference value. Furthermore, elapsed-time-information acquisition means for acquiring an elapsed time from the initiation of the digital data capturing operation by the data capture means is primarily composed of the control device 10.

The control device 10 serving as the reference-value change means is operable to add the acquired elapsed time to the basic count value as a predetermined reference value for count values so as to obtain an adjusted reference value.

Thus, the apparatus according to the fourth embodiment can change the reference value depending on elapsed times from initiation of the measurement in a significant simple manner of adding the acquired elapsed time to the predetermined reference value, so as to absorb adverse affects of load variations due to shapes or tremors during a body weight measurement for an elderly or overweight user who has difficulty in maintaining an adequate measurement posture, or due to external environments, such as uneven surface or vibrations of a floor having the digital measurement apparatus placed thereon, to avoid a measurement error and quickly compete the measurement. The apparatus according to the fourth embodiment can be widely used as various digital weight measurement apparatuses for measuring the weight of a variety of articles, as well as body weight While the digital measurement apparatus of the present invention and the specific embodiments thereof have been shown and described in detailed, it is obvious to those skilled in the art that various changes and modifications may be made in the specific embodiment as long as they meet the structural requirement as set forth in appended claims.

For example, information about age to be acquired by the age-information acquisition mean in the first and third embodiments is not limited to the age itself of a user, but may be a rough age classification. Specifically, the rough age classification may include a classification consisting of a first age group less than 50, a second age group ranging from 50 to less than 70, and a third age group equal to or greater than 70. The rough age classification may also include a classification consisting of an average adult and an elderly person. As means for acquiring such a rough age classification, it is contemplated to provide a dedicated button (button dedicated to elderly persons) capable of being readily pushed down by a user. This dedicated button incorporated in a digital body-weight or body-composition measurement apparatus implementing the present invention would be conveniently used, particularly, in a group medical examination of elderly persons.

The reference-value change means in the first and third embodiments is not limited to the aforementioned specific type designed to add or subtract the user's age to or from a single predetermined reference value, but may be another type designed to select and use one of a plurality of predetermined reference values corresponding to ages or age groups, depending on the user's age. For example, reference values A, B and C are selected and used, respectively, when the user's age is less than 50, when the user's age is in the range of 50 to less than 70, and when the user's age is equal to or greater than 70.

Further, the reference-value change means is not limited to the aforementioned specific type designed to change the reference value in accordance with the user's age or body weight, or the elapsed time from initiation of the measurement, but may be another type designed to change the reference value in response to a command entered more directly by a user. In this case, the reference-value change means may include change-intention entry means for allowing a user to enter a command indicative of a user's intention of changing the reference value. Specifically, it is contemplated to provide a dedicated button (a simplified-measurement button etc.) capable of being readily pushed down by a user. This dedicated button incorporated in a digital weight measurement apparatus implementing the present invention would be convenient, particularly, when the digital weight measurement apparatus is used in circumstances having thumping vibrations, such as vehicles.

What is claimed is:

1. A digital measurement apparatus including data capture means operable to continuously capture digital data about a body weight of a user, validity determination means operable to compare said captured data with a reference value so as to determine whether all of said captured data are valid, and measurement-value calculation means operable, when all of said captured data are determined to be valid, to calculate a measurement value in accordance with said valid data, said digital measurement apparatus being characterized by further comprising reference-value change means operable to change said reference value, wherein said reference-value change means includes age-information acquisition means for acquiring information about said user's age, and wherein said reference-value change means is operable to change said reference value in accordance with said acquired age information to add or subtract the user's age to or from said reference value.

2. A digital measurement apparatus including data capture means operable to continuously capture digital data about a body weight of a user, validity determination means operable to compare said captured data with a reference value so as to determine whether all of said captured data are valid, and measurement-value calculation means operable, when all of said captured data are determined to be valid, to calculate a measurement value in accordance with said valid data, said digital measurement apparatus being characterized by further comprising reference-value change means operable to change said reference value, wherein said reference-value change means includes age-information acquisition means for acquiring information about said user's age, and wherein said reference-value change means is operable, when the user's age contained in said acquired age information is equal to or greater than a given age, to change said reference value in accordance with said acquired age information to add or subtract the user's age to or from said reference value.

3. A digital measurement apparatus including data capture means operable to continuously capture digital data about a body composition of a user, validity determination means operable to compare said captured data with a reference value so as to determine whether all of said captured data are valid, and measurement-value calculation means operable, when all of said captured data are determined to be valid, to calculate a measurement value in accordance with said valid data, said digital measurement apparatus being characterized by further comprising reference-value change means operable to change said reference value, wherein said reference-value change means includes age-information acquisition means for acquiring information about said user's age, and wherein said reference-value change means is operable to change said reference value in accordance with said acquired age information to add or subtract the user's age to or from said reference value.

4. A digital measurement apparatus including data capture means operable to continuously capture digital data about a body composition of a user, validity determination means operable to compare said captured data with a reference value so as to determine whether all of said captured data are valid, and measurement-value calculation means operable, when all of said captured data are determined to be valid, to calculate a measurement value in accordance with said valid data, said digital measurement apparatus being characterized by further comprising reference-value change means operable to change said reference value, wherein said reference-value change means includes age-information acquisition means for acquiring information about said user's age, and wherein said reference-value change means is operable, when the user's age contained in said acquired age information is equal to or greater than a given age, to change said reference value in accordance with said acquired age information to add or subtract the user's age to or from said reference value.

* * * * *